United States Patent [19]

Kennedy et al.

[11] Patent Number: 5,185,809
[45] Date of Patent: Feb. 9, 1993

[54] MORPHOMETRIC ANALYSIS OF ANATOMICAL TOMOGRAPHIC DATA

[75] Inventors: David N. Kennedy, Boston; Pauline A. Filipek, Brighton; Verne S. Caviness, Jr., Charlestown, all of Mass.

[73] Assignees: The General Hospital Corporation, Boston; Massachusetts Institute of Technology, Cambridge, both of Mass.

[21] Appl. No.: 511,334

[22] Filed: Jun. 7, 1990

Related U.S. Application Data

[60] Division of Ser. No. 100,996, Sep. 25, 1987, Pat. No. 4,961,425, which is a continuation-in-part of Ser. No. 85,576, Aug. 14, 1987, abandoned.

[51] Int. Cl.$^5$ .............................................. G06K 9/78
[52] U.S. Cl. ........................................ 382/6; 382/18; 382/22; 382/43; 364/413.13; 128/653.1
[58] Field of Search ...................... 382/6, 18, 22, 43; 364/413.13

[56] References Cited

U.S. PATENT DOCUMENTS 4,839,807  6/1989  Doi et al. ................................ 382/6
4,856,528  8/1989  Yang et al. ......................... 382/6 X

OTHER PUBLICATIONS

Rossnick et al. "Three-Dimensional Display of Blood Vessels In Magnetic Resonance Imaging," *Computers in Cardiol.*, 201-204, (Oct. 1986).
Kennedy et al., "Three-Dimensional Display from Cross-Sectional Tomographic Images: An Application to Magnetic Resonance Imaging," *IEEE Trans. on Med. Imaging*, vol. MI-6, No. 2, pp. 134-140 (Jun. 1987).
Condon et al., "A Quantitative Index of Ventricular and Extraventricular Intracranial CSF Volumes Using MR Imaging," *Journal of Computer Assisted Tomography* 10(5), pp. 784-792 (1986).
Zhu et al., "Accuracy of Area Measurements Made from MR Images Compared with Computed Tomography", *Journal of Computer Assisted Tomography* 10(1), pp. 96-102 (1986).
Sechtem et al., "Measurement of Right and Left Ventricular Volumes in Healthy Individuals with Cine MR Imaging$^1$," *Radiology*, 163:3, pp. 697-702 (Jun. 1987).

(List continued on next page.)

*Primary Examiner*—William E. Kamm
*Assistant Examiner*—Brian L. Casler
*Attorney, Agent, or Firm*—Fish & Richardson

[57] ABSTRACT

A system for automatically determining the outline of a selected anatomical feature or region (e.g., in a slice of magnetic resonance data) and then making a quantitative determination of a morphometric parameter (such as area or volume) associated with the feature. A volumetric measurement of the feature is made by determining for each slice the areas within the outline for the feature and summing the areas for all the slices; the outlines are based on intensity contours, where the intensity of the contour is intermediate that within and outside of the feature; the intermediate intensity is chosen objectively based on a histogram of intensity levels; interpolation is used to assign contour locations in areas where the intensity of the contour is not present exactly; the accuracy of the outline is improved using an edge-optimization procedure in which the outline is shifted transversely to the location at which an estimate of the derivative (e.g., the Sobel operator) is a maximum; an alternative technique for choosing the initial outline is to examine the drop or rise in intensity along a radial direction from a starting point within the region of interest and assign the contour to the location at which the difference in intensity reaches a predetermined value; the optimized outline for the first slice of data is saved and used as the initial outline for the adjoining slice, and the procedure of adjusting the outline transversely to the location at which a derivative estimate is a maximum is repeated, and so on, until outlines have been generated for all slices.

9 Claims, 12 Drawing Sheets

Microfiche Appendix Included
(105 Microfiche, 2 Pages)

Rehr et al., "Left Ventricular Volumes Measured by MR Imaging[1]," *Radiology,* 156:3, pp. 717–719 (Sep. 1985).

Graf et al., "A New Method in Computer-Assisted Imaging in Neuroanatomy[1]" Acta anat. vol. 123, pp. 240–246 (1985).

Ehrlich et al., "The Origin of Shape Frequency Distributions and the Relationship Between Size and Shape[1]," *J. Sedim. Petrol,* 50(2) pp. 475–484 (Jun. 1980).

Ehrlich et al., "An Exact Method For Characterization of Grain Shape[1]" *J. Sedim. Petrol,* vol. 50 No. 1, pp. 205–212 (Mar. 1970).

Healy, G., Sanz, J. L. C., "Contam: An Edge-based Approach To Segmenting Images With Irregular Objects" *IEEE Conf. on Comp. Vision and Pattern Recognition,* 1, 485, pp. 485–489 (1985).

Twogood et al., "Digital Image Processing," *IEEE Transactions on Nuclear Science,* vol. NS-29, No. 3, pp. 1076–1086 (Jun. 1982).

Durrington et al., "The Assessment of Achilles Tendon Size in Primary Hypercholesterolaemia by Computed Tomography," *Atherosclerosis,* 45 pp. 345–358 (1982).

Chow et al., "Boundary Detection and Volume Determination of the Left Ventricle from a Cineangiogram", *Computers in Biology and Medicine* vol. 3, pp. 13–26 (1973).

Wakabayashi et al., "Shimazu Nuclear Medicine Data Processing System, Scintipac Series," *Shimazu Journal,* Dec. 1978.

Fox et al., "A Stereotactic Method of Anatomical Localization for Positron Emission Tomograph," *Journal of Computer Assisted Tomography,* vol. 9, No. 1, pp. 141–152 (1985).

Maguire et al., "Correlation Methods for Tomographic Images Using Two and Three Dimensional Techniques," in Info. Process. in Med. Imag. (Proceedings of the 9th IPMI Conference), Martinus Nijhoff Pub., pp. 266–279 (1986).

Kessler et al. in Front. Radiat. Ther. Onc., vol. 21, pp. 25–32 (1987).

MORPHOMETRIC ANALYSIS OF ANATOMICAL TOMOGRAPHIC DATA

This is a divisional Ser. No. 07/100,996 filed Sep. 25, 1987 now U.S. Pat. No. 4,961,425, which is a continuation-in-part of application, Ser. No. 085,576, filed on Aug. 14, 1987, now abandoned.

REFERENCE TO MICROFICHE APPENDIX

The application includes a microfiche appendix pursuant to 37 CFR section 1.96(b) containing 2 microfiches having 105 frames.

BACKGROUND OF THE INVENTION

This invention relates to morphometric analysis of anatomical tomographic data, e.g., in vivo volumetric measurement of regions of the human brain.

Precise quantitative volumeric measurements of central nervous system morphology are necessary to obtain objective assessments of major nuclear structures and gray-white matter abnormalities involved in various disease processes. Numerous in vitro quantitative techniques are currently available for evaluation of brain morphology, but these are limited to use in postmortem tissue, often leading to error from the unpredictable variability in tissue fixation procedures. A specific method of in vivo quantitative analysis of brain morphology has not previously been available. Morphometric reconstruction from computerized tomographic data has been limited because of relatively low resolution, and X-ray scatter at bony interfaces.

Prior efforts at morphometric analysis of tomographic data have tended to rely on manual procedures. For example, feature outlines have been drawn by hand; areas have been determined by projecting a tomographic image onto a wall on which graphical divisions appear and manually counting squares within the region of interest; outlines have been drawn manually by cursor movement on computer displays, with attendant inaccuracy and tedium; volumetric measurements have been roughly estimated based on two-dimensional measurements and assumptions about the shape of the feature (e.g., that it remains an ellipsoid).

Tomographic images of the body tend to be difficult candidates for image processing because the boundaries between regions are not sharply defined, and because there are sometimes large variations in intensity within regions. The difficulty is especially pronounced in the case of selecting a boundary between adjoining regions of soft tissue (e.g., between the cortex and white matter of the brain).

Improved morphometric analysis techniques may be useful in recognizing regions of abnormality in patients suffering from disorders, e.g., developmental language disorders (DLD or dysphasia) and autistic spectrum disorders (ASD), for which no abnormalities are typically observable from mere visual interpretation of MRI scans.

SUMMARY OF THE INVENTION

We have discovered an efficient, computerized technique for performing morphometric analysis of anatomical tomographic data. The invention permits in vivo morphological analysis of anatomical features, both normal and pathologic. It is of particular benefit in making volumetric measurements of selected regions of the brain. The measurements can be made in a matter of hours, and with high accuracy. Subjective determination of outlines and feature locations, essential in prior techniques, are largely eliminated.

In general the invention features, in a first aspect, automatically determining the outline of a selected anatomical feature or region (e.g., in a slice of magnetic resonance data) and then making a quantitative determination of a morphometric parameter (such as area or volume) associated with the feature. In preferred embodiments, a volumetric measurement of the feature is made by determining for each slice the areas within the outline for the feature and summing the product of the areas and their respective thicknesses for all the slices; the outlines are based on intensity contours, where the intensity of the contour is intermediate that of the intensity of pixels within the feature and the intensity of pixels outside of the feature; the intermediate intensity is chosen objectively based on a histogram of intensity levels; interpolation is used to assign contour locations in areas where the intensity of the contour is not present exactly; the accuracy of the outline is improved using an edge-optimization procedure in which the outline is shifted transversely to the location at which an estimate of the derivative (e.g., the Sobel operator) is a maximum; an alternative technique for choosing the initial outline is to examine the drop or rise in intensity along a radial direction from a starting point within the region of interest and assign the contour to the location at which the difference in intensity reaches a predetermined value; the optimized outline for the first slice of data is saved and used as the initial outline for the adjoining slice, and the procedure of adjusting the outline transversely to the location at which a derivative estimate is a maximum is repeated, and so on, until outlines have been generated for all slices.

The quantitative volumetric measurements made possible by the invention will be of particular value in early diagnosis of disease, prior to clinical manifestations. For example, decreases in cortex volume of a few percent, indicative possibly of certain childhood brain disorders, are detectable by the invention. The invention is expected to make possible accurate and early detection of the effect of chemotherapy on tumors. Subjective evaluation of reduction in tumor size is not generally possible until a reduction of about 30% has occurred, and even then subjective determinations vary widely. Small bits of cortex can be lost in each slice, and escape notice in a subjective review. The invention should be able to detect volumetric changes of just a few percent, and the cumulative effect of small changes in different slices is readily detected. The invention permits measurement of absolute volume in cubic centimeters, instead of ratios. This allows determination of brain volume occupied by particular features, e.g., the ventricles, information that may be of great clinical usefulness.

In a second aspect, the invention features automatically identifying and mapping, within a given feature or region, zones of abnormal inhomogeneities in tissue composition. In preferred embodiments, the zones of abnormality are those areas in which the signal intensity (either T1 or T2 weighted) is more than two standard deviations from the mean of the distribution of the normal population (i.e., more than two normal standard deviations from the mean); the intensity distribution of a normal structure (which experience has shown follows a unimodal Gaussian distribution) is derived from intensity histograms (in which the number of pixels at a given intensity is plotted as a function of intensity). Intensity histograms are prepared for selected features, and compared to histograms of the same features from normal individuals; differences in the mean and standard deviation of a patient's intensity distribution from the intensity distribution of the normal population provides clincally useful information.

In a third aspect, the invention features applying a standardized spherical three-dimensional coordinate system to the brain to allow anatomic features of the brain to be characterized in terms of their location and orientation. In preferred embodiments, the landmarks used for standardizing the coordinate system are the midpoint of decussation of the anterior commissure (which is used as the origin), the midpoint of crossing of the posterior commissure, and the midpoint of the genu of the corpus callosum; also useful as reference landmarks are principal and secondary fissures, such as angular and supramarginal gyri, planum temporale, first temporale convolutions, and Sylvian opercula. Any contoured cerebral structure or focal lesion/zone or inhomogeneity within the forebrain, indeed any anatomical landmark such as a gyrus or fissure, may be characterized in terms of its projection within the standardized coordinate system.

In a fourth aspect, the invention features characterizing anatomical features (e.g., regions of abnormal inhomogeneity) by their three-dimensional shape, using spatial Fourier frequency distribution analysis, with control brain images providing the normal range of variance.

The routines for mapping inhomogeneities and for characterizing the shape, location, and orientation of anatomical features are completely automated and independent of investigator interaction.

The invention is capable of detecting subtle morphometric abnormalities in specific gyri or individual Brodmann's areas of cerebral cortex, and promises to further localize etiology. As well, it can be utilized in the morphometric evaluation of normal growth patterns of the developing brain in children, or of disorders of altered brain growth, previously unavailable premortem. It has the potential of identifying substructural morphometric phenotype in presymptomatic neurodegenerative diseases lacking genotypic identification, producing a means for presymptomatic or carrier diagnosis. There are many potential clinical uses for the invention as an adjunct to clinical MRI interpretations: sequential volumetric analyses of mass lesions, inflammatory or degenerative processes within the brain would provide sufficient sensitivity to identify subtle but significant changes in volume which might otherwise not be appreciated. Indeed, this methodology has potential clinical applications to the volumetric analysis of any structure or lesion which can be visualized by MRI.

The invention provides more precise identification and quantification of subtle neurologic disease progression. Presymptomatic white matter lesions of multiple sclerosis may be recognized only as the result of signal intensity deviations, potentially leading to earlier presymptomatic treatment prior to the occurrence of irreversible damage. In adrenoleukodystrophy, an example of an inherited neurodegenerative disease, the "advancing edge" of white matter destruction in florid disease is conventionally determined by visual inspection and potentially overshadows more subtle areas of early white matter destruction. These previously unrecognized areas are theoretically the sole disease in unidentified presymptomatic individuals. Their identification would provide a quantitative evaluation of the efficacy of presymptomatic and symptomatic experimental therapeutic trials. At postmortem examination, brain tumor tissue often extends beyond those borders conventionally recognized by magnetic resonance imaging modalities. Recognition and measurement of this subtle tumor expansion would potentially initiates more aggressive therapy and objectively determine therapeutic response.

The invention provides the first opportunity to spatially characterize the overall living brain, as well as its component substructures. It permits an evaluation of the complicated relationship between shape, volume and geometry of the living human brain. It characterizes the normal variation in global and regional brain shape in living individuals and identifies the normal deviations. As a result, it substantially increases the understanding of neuroanatomic relationships, which are generally recognized but have not been precisely determined.

The invention permits comparison of study populations with specific disease entities or developmental disabilities to identify pathologic distortions, some of which may prove to be syndrome-specific, or at least characteristic. At a minimum, distortions of hemispheric symmetry will become readily evident by this analysis. Shape and size variations may become apparent which are neither related to a tissue reductive process, nor a direct reflection of focal lesions. Abnormal degrees of variation in the shape or geometric relationships of structures in the two hemispheres would emerge if they exist, potentially in regions which are remote from focal abnormalities.

Other features and advantages of the invention will be apparent from the following description of a preferred embodiment and from the claims.

DESCRIPTION OF THE PREFERRED EMBODIMENT

Drawings

FIG. 1 is a diagrammatic rendering of the appearance of a slice of magnetic resonance data; shading has been used to suggest the variations in intensity of the atrial tomographic image; (the darkest areas of the image, such as the ventricles, are shaded with closely spaced lines; gray areas, such as the cerebral and cerebellar cortex, are shaded with dots; the white matter has no shading; in the actual image shading is much more varied and irregular). Slightly more than half of the drawing shows the computer-generated outlines (dark lines) generated by a preferred embodiment of the invention.

FIGS. 4, 5A, 5B, 6A, 6B, 7A, 7B, 8, 9A, and 9B are flow charts of the software of said embodiment.

SYSTEM

A Digital Equipment Corporation VAX 11/750 computer system with color monitor capable of displaying 512×512 pixels (e.g., Sony Trinitron with Datacube QVG—123 frame buffer) is used to process magnetic resonance image (MRI) data received on magnetic tape from a high resolution, thin slice nuclear magnetic resonance (NMR) system (e.g., the Siemens 1.0 Tesla Magnetom MR System operated with a FLASH (Fast Low Angle Shot) three-dimensional gradient echo pulse sequence, TR =40 msec, TE=15 msec, SL=3.1 mm). The MRI data providing the best contrast of the features of interest is used; generally the T1-weighted image is preferred for volumetric studies. Both T1 or T2-weighted images are useful for mapping zones of abnormal inhomogeneity. User interaction with the system is accomplished with a Sumagraphics MM1201 digitizing tablet with mouse, and a Digital Equipment Corporation VT 100 terminal.

The frame buffer provides high-speed, high resolution video acquisition, storage, and display. The digitizing tablet provides a user interface for video cursor driving, menu selection, and two-dimensional digitization; interaction is performed with either a stylus or a four-button cursor.

The software embodying the invention is listed in the accompanying appendix (FORTRAN source code listings). A list of the programs, with short descriptions of each, appears in a table at the end of the specification. FIGS. 4-9B are flow charts of the principal programs.

The software provides a semi-automated means of choosing outlines (or boundaries) of selected anatomical regions (or features), and of then automatically computing the volumes of the selected regions.

Figure 4:
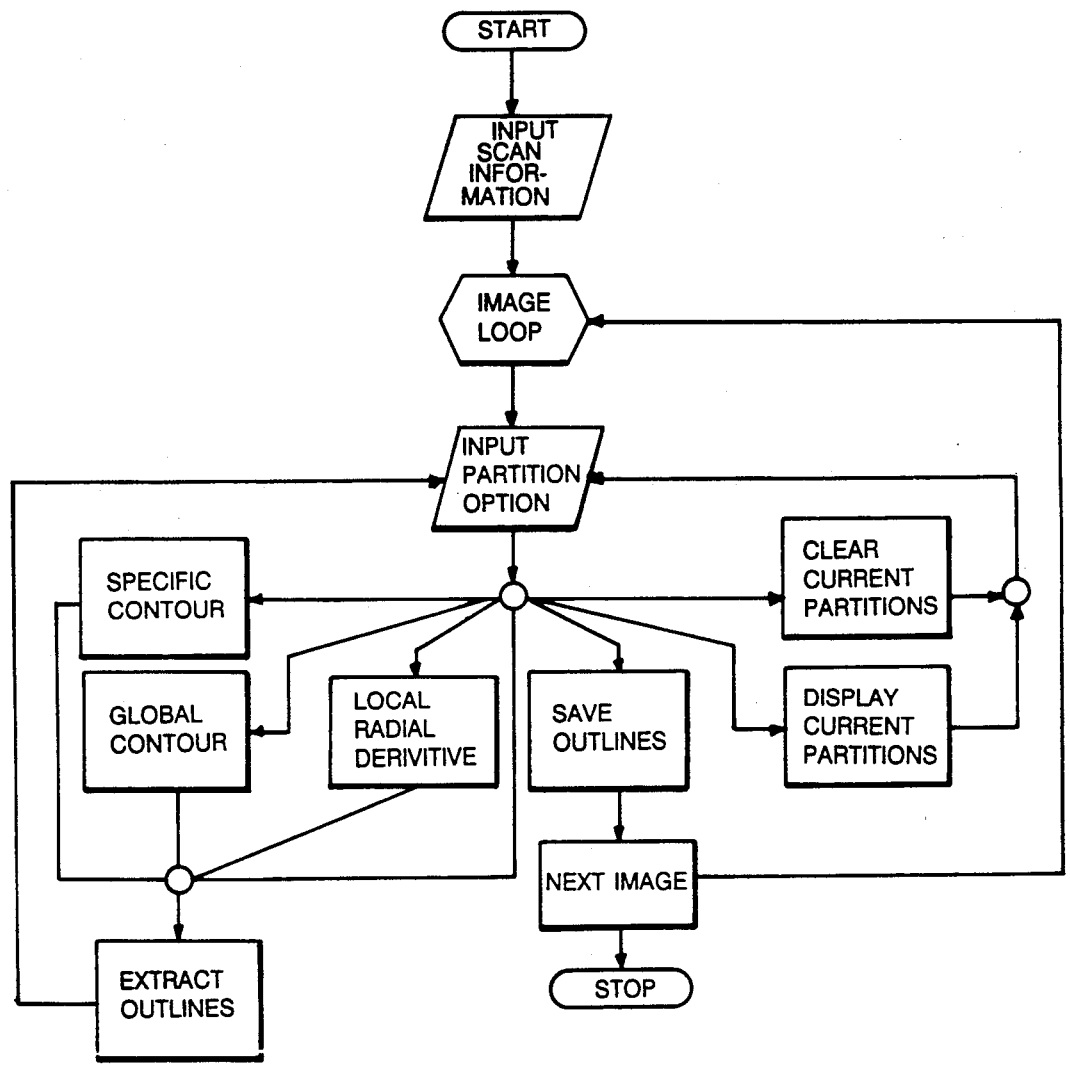
Figure 5A:
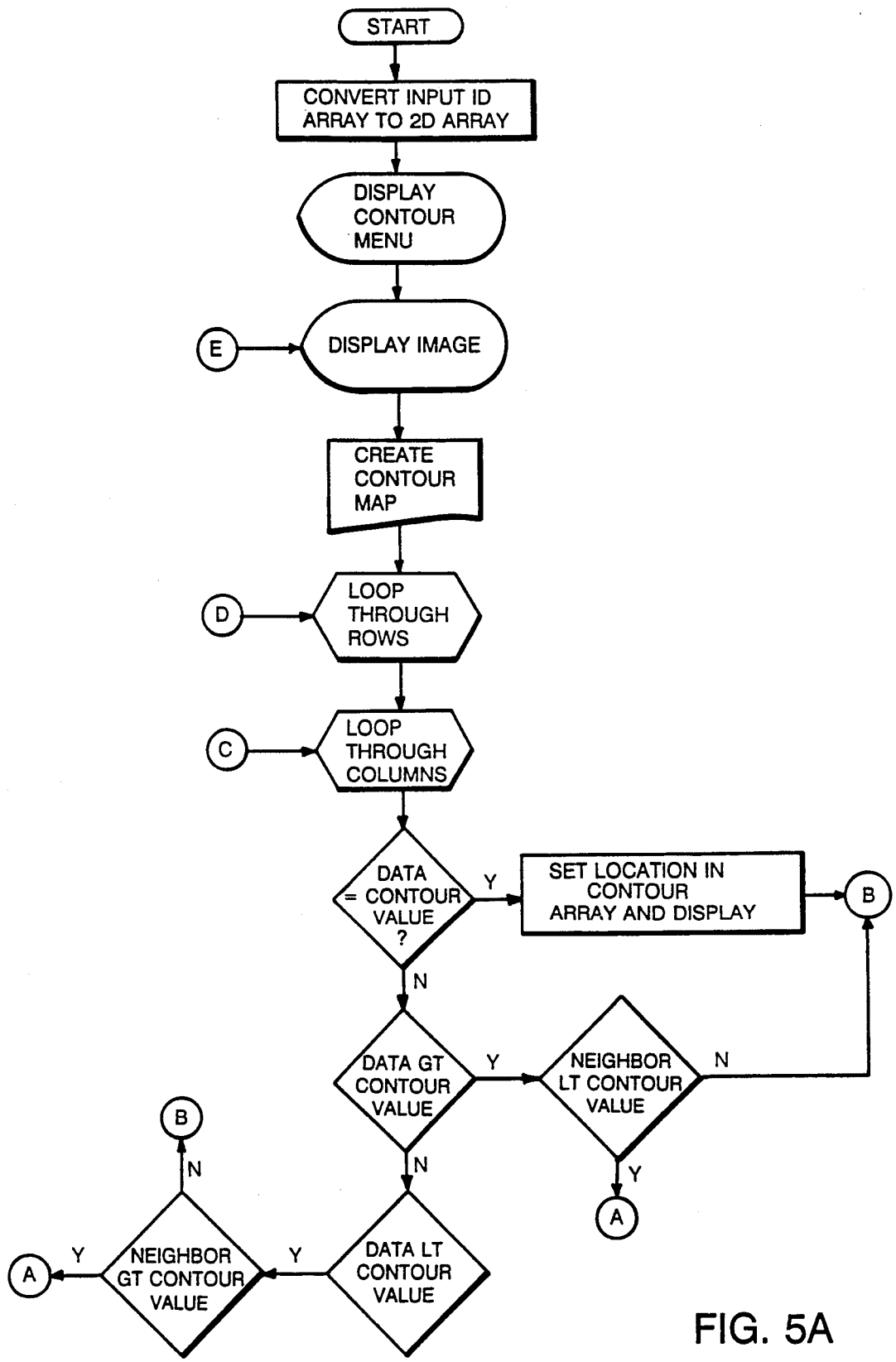
Figure 5B:
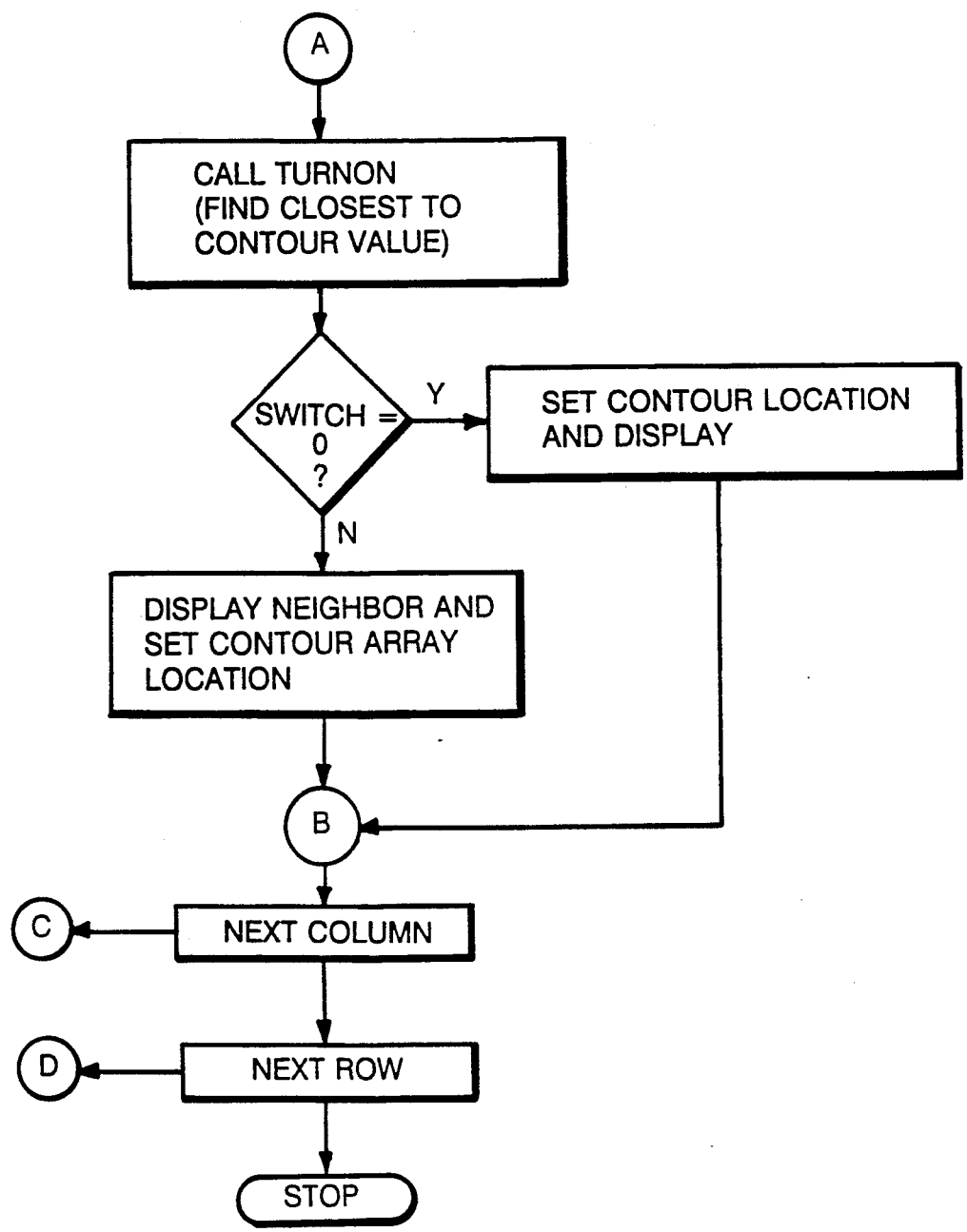

FIG. 4 is an overall flow chart of the program (FINAL) used to generate initial outlines. Magnetic resonance data ("scan information") are read from magnetic tape. The data are displayed as a 512×512 image with 256 gray levels (0 to 255). The user generates initial outlines of selected features using tools selected from a menu (block labelled "input partition option", and blocks below it).

One menu option is to use intensity contours as the initial outlines. The user moves the cursor to a pixel at the outer edge of a selected anatomical feature (e.g., the cortex), and instructs the program to display one or all contours having the intensity of the selected location. CONT2 produces all such points in the image by doing a full scan of the entire image (block labelled "global contour"). SCONT produces only the contour on which the cursor has been positioned, by moving point by point around the contour until returning to the starting point (block labelled "specific contour"). The choice of intensity contour can be made in this manual way, or it can be made automatically using a histogram to provide an estimate of the intensity at the outline separating two regions (see below).

After the outermost contour has been generated, subprogram HFILL2 counts the number of pixels within the outline (to provide an area measurement) and generates a histogram (i.e., a plot of the number of pixels at each intensity level between 0 and 255 versus the intensity level). For the human brain, the histogram generally exhibits three main peaks—one for the black of the ventricles, another for the gray of the cortex, and another for the white of the white matter. The peaks are separated by valleys. The minimum point in a valley provides a reasonably accurate (and objective) estimate of the intensity level corresponding to the boundary or outline between two neighboring regions. Thus, the intensity contour used as the initial outline between the cortex and white matter preferably has the intensity level of the valley between the histogram peaks corresponding to the gray and white intensities of the cortex and white matter. After the cortex/white matter boundary is generated, the procedure of counting pixels and generating a histogram is repeated; this provides an intensity level for generating the outlines of the ventricles.

Another menu option is to generate the initial outline using a radial differential technique. This technique is useful for outlining regions such as the caudate nucleus, where the change in intensity at the boundary varies tremendously along the outline; e.g., the caudate nucleus borders on one side the white matter and on the other the ventricle, and thus at its boundary the transition is sometimes from white to gray and other times from gray to black. This makes it impossible to use an intensity contour to choose the initial outline because the intensity at the gray/black transition is very different from the intensity at the white/gray transition.

Subprogram RAD chooses an outline by moving out radially from a cursor-chosen location within a selected region (e.g., within the caudate nucleus) to find the pixel at which there is at least a predetermined difference (either positive or negative) from the intensity at the center of the region. The predetermined difference is preferably some predetermined number of standard deviations. This radial differential procedure is followed for a full 360° around the selected location, to produce the initial outline. In the case of the caudate nucleus, the center of the nucleus might have an intensity of 100 (on the 0-255 gray scale), and the outline might be chosen as that location where pixel intensity differs by as much as 20 (i.e., either 80 or 120).

Any gaps in the outlines generated by the intensity contour and radial differential techniques can be filled manually or by automatic interpolation.

Interpolation is also used to assign the contour to appropriate pixels in those regions where the selected intensity (or intensity difference) does not exactly occur (For example, where adjacent pixels have intensity values in the range from 31 to 35, but none has exactly the chosen contour intensity of 33, the contour would be assigned to the pixel having the intensity closest to 33.

The software also permits the user to manually draw portions of the outlines using a digitizing tablet. This can be necessary in regions of the image where neither the intensity contour or radial differential techniques will produce a reasonable outline.

Other menu options are used to extract selected outlines from the image (subprogram EDGEXT extracts the specific outline surrounding the location of the cursor) and to erase, display or save outlines. The EDIT subprogram (executed within the block labelled "NEXT IMAGE") allows the user to go through all of the outlines previously saved and delete any of them or modify the labels of the regions they outline.

Figure 1:
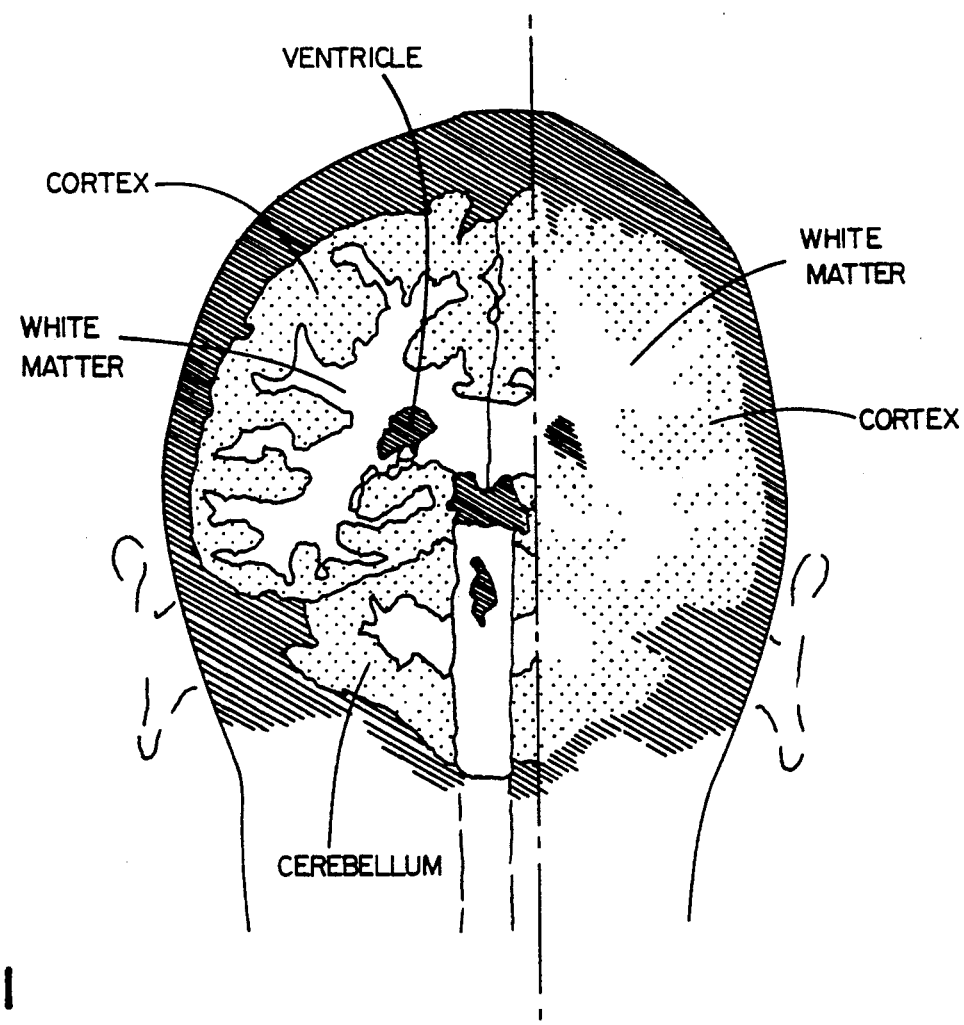

FIG. 1 shows diagrammatically the outlines generated by the software. The raw MRI data, prior to generation of the outlines is shown in the right portion of the figure. The computer-generated outlines have been added to the left portion; the outlines are the solid lines dividing the differently-shaded regions, e.g., cortex, white matter, ventricles, and cerebellum. It has not been possible, given the limitations of inked drawings, to convey accurately the intensity variations in the MRI data.

In a typical analysis the FINAL program is used to generate initial outlines for a single slice. Control is then passed to AUTO3 (flow chart shown in FIGS. 7A, 7B), which improves the initial outlines using an edge predicting operator known as the Sobel operator. Pratt, W. K., *Digital Image Processing*, John Wiley & Sons (1978). The outlines generally need to be improved because substantial error can result, at least at some points on the outline, from relying solely on an intensity level (or difference in intensity) to define the outline. It is very often the case with MRI data that the intensity level at a boundary will vary at locations along the boundary; this can happen-, for example, if the intensity level of a dark, surrounding region varies from the top to the bottom of the image, as can happen with MRI data; in such a case, an intensity level that fell squarely on the boundary between the adjoining regions in one part of the image may be substantially distant from the boundary at another part of the image. Another difficulty with relying on absolute intensity (or a constant differential) is that within a region there can be substantial noise and other variations in intensity, leading to errors in outline location if this noise or variation is close to the outer boundary of the region.

Figure 8:
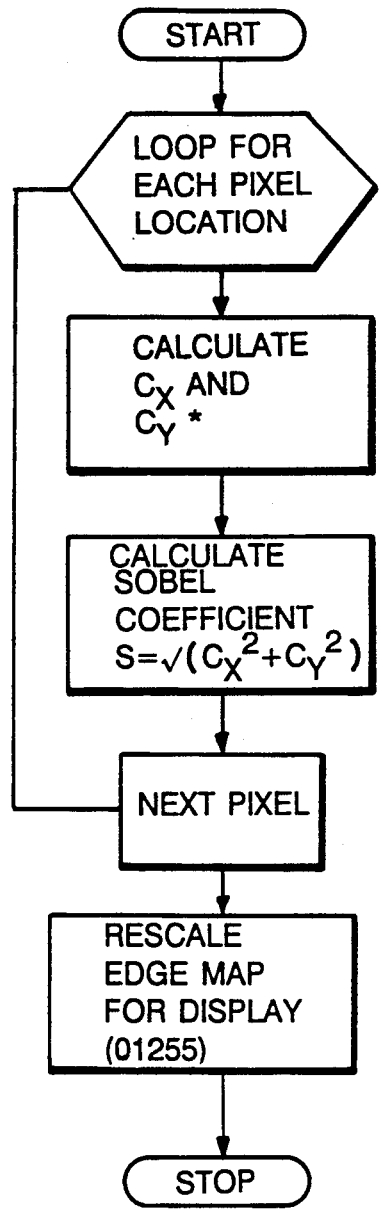

Subprogram SOBSUB generates a map of the Sobel operator according to the expressions shown in FIG. 8. Each point in the Sobel-operator map represents a measure of the differential change over the 3×3 pixel area surrounding that point. $C_x$ is a measure of the differential in the x direction, and $C_y$ a measure in the y direction. The Sobel operator is the root mean square of these two measures.

Figure 9A:
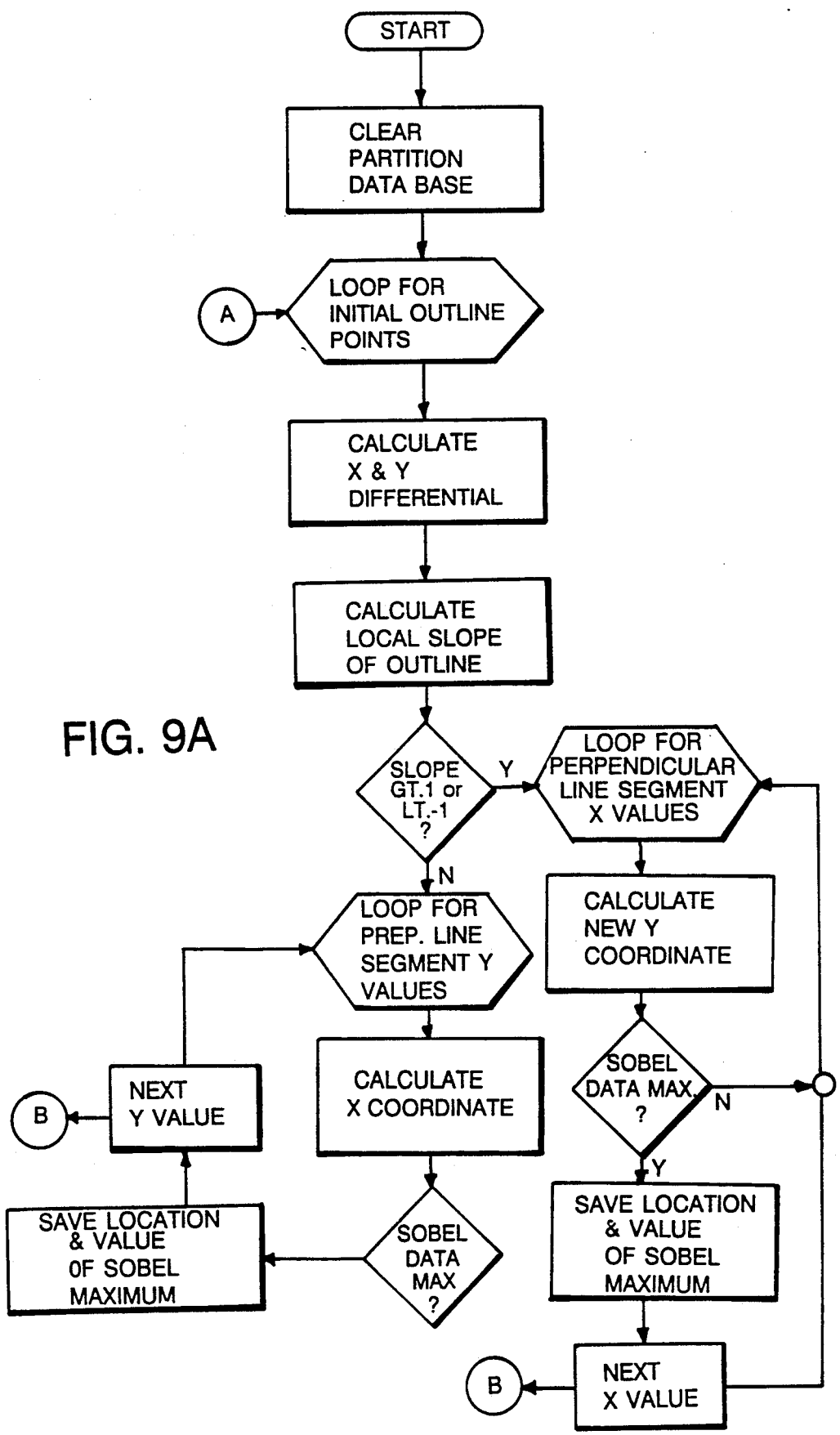
Figure 9B:
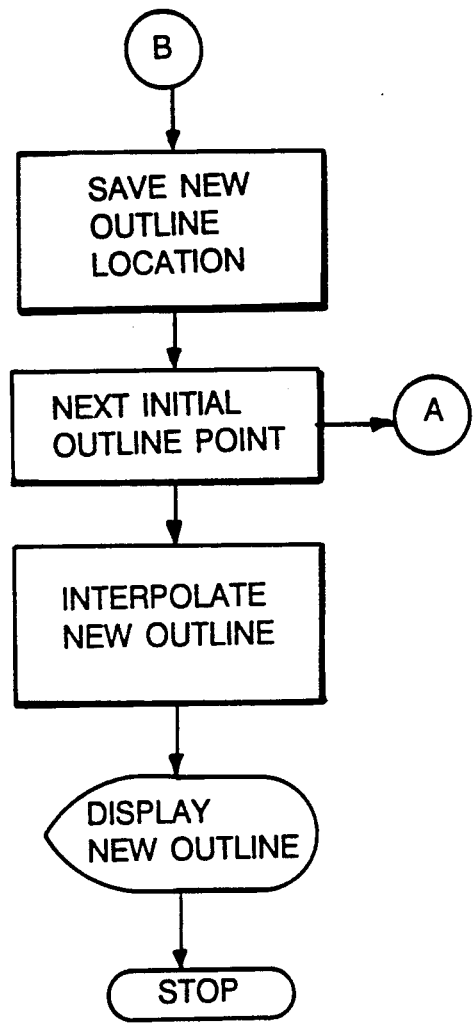

After the Sobel-operator map has been generated, each initial outline is optimized at each point along its path by shifting the location of the outline transversely to the point at which the Sobel operator is at a maximum. This is accomplished by moving along a direction normal to the outline (e.g., line N in FIG. 2) and determining along that normal path the location at which the Sobel operator is at a maximum. FIG. 3 is an illustration of how the variation in Sobel operator might appear at a typical point where the initial outline required substantial realignment. The point at which the Sobel operator is at a maximum is 4 pixels inward from the location of the initial outline, and, therefore, the final outline is assigned to that new pixel location. Limits (such as 8 pixels in each direction) are placed on how far along the normal path the search for the Sobel maximum will extend. This procedure, which is described by the flow chart of FIGS. 9A and 9B, is repeated at each point along each outline.

An alternative to the Sobel optimization procedure is to examine simply the derivative (or slope) of intensity in the normal direction at each point along the normal path. Both this approach and the preferred Sobel one are broadly similar in that both choose the new outline location based on a measure of the derivative of the intensity, but the Sobel operator, because it bases its derivative measurement on a larger area (3×3 pixels), does a better job of optimizing the boundary location.

Figure 2:
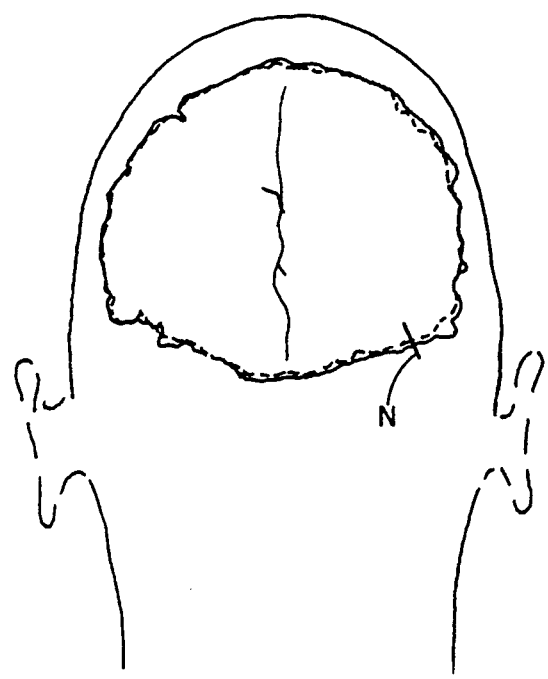
FIG. 2 is a further diagrammatic rendering of a slice of magnetic resonance data, showing the initial (solid line) and optimized (dashed line) outlines generated by said embodiment for the outer boundary of the cortex.
Figure 3:
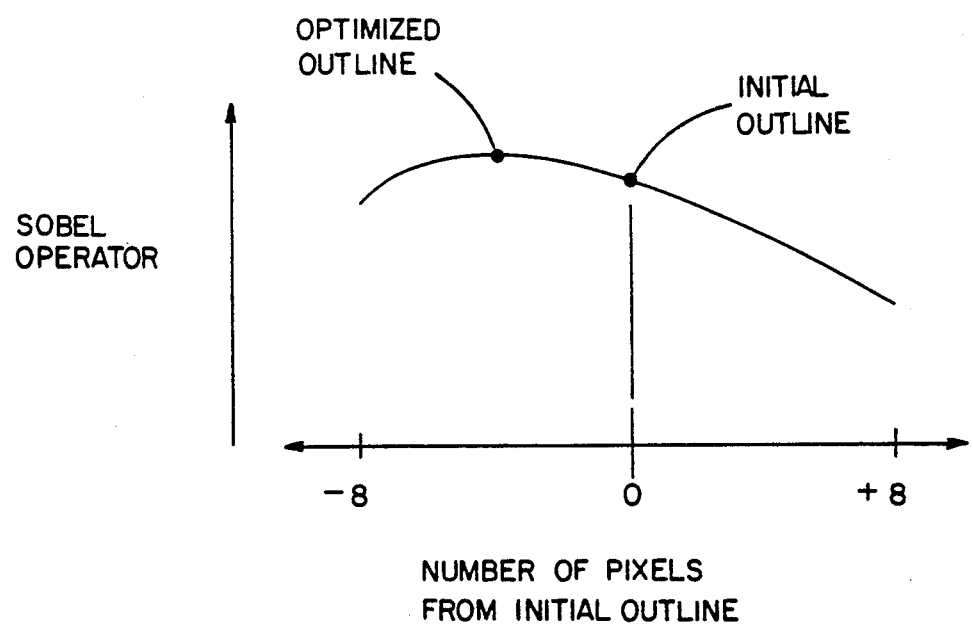
FIG. 3 is a diagrammatic plot of variation in the edge predicting operator along normal line N in FIG. 2.

FIG. 2 provides a diagrammatic illustration of the effect of the Sobel edge optimization. The solid line represents the initial outline chosen on the basis of intensity alone. The dashed line represents the optimized outline chosen on the basis of the Sobel edge optimization.

After AUTO3 has optimized the initial outlines for the first slice of MRI data, the optimized outlines are stored (FIG. 7B) for use on the next slice. Because the slice thickness is small (preferably 3 mm, but 8 mm can be used), there is generally only a small change in the location of the outlines between adjacent slices. This fact can be used to advantage by using as the starting point for optimization in any given slice the optimized outline in the prior slice. This avoids the need to repeat the outline generation steps of the FINAL program at each slice. Only the Sobel operator optimization needs to be repeated. A map of the Sobel operator for the new slice is generated, and the point-by-point realignment of the outlines to the Sobel maxima along normal lines is done for each point on each outline. This procedure is repeated until all the slices have been assigned final, optimized outlines.

After each stage at which an outline is optimized by the Sobel operator, a check is made of the new outline to be sure that it does not contain any glitches or spikes as the result of a failure of the optimization. The check is performed by generating at each pixel on the outline (using a moving average) the mean and standard deviation for one-eighth of the outline centered on the pixel in question. If the intensity at the pixel is more than two standard deviations from the mean, the pixel is excluded from the outline. It is not unusual to have to exclude many pixels (e.g., approaching half the total pixels) from each outline as a result of this checking. The gaps left by these rejected points are filled by ordinary straight line interpolation between the remaining points.

Figure 6A:
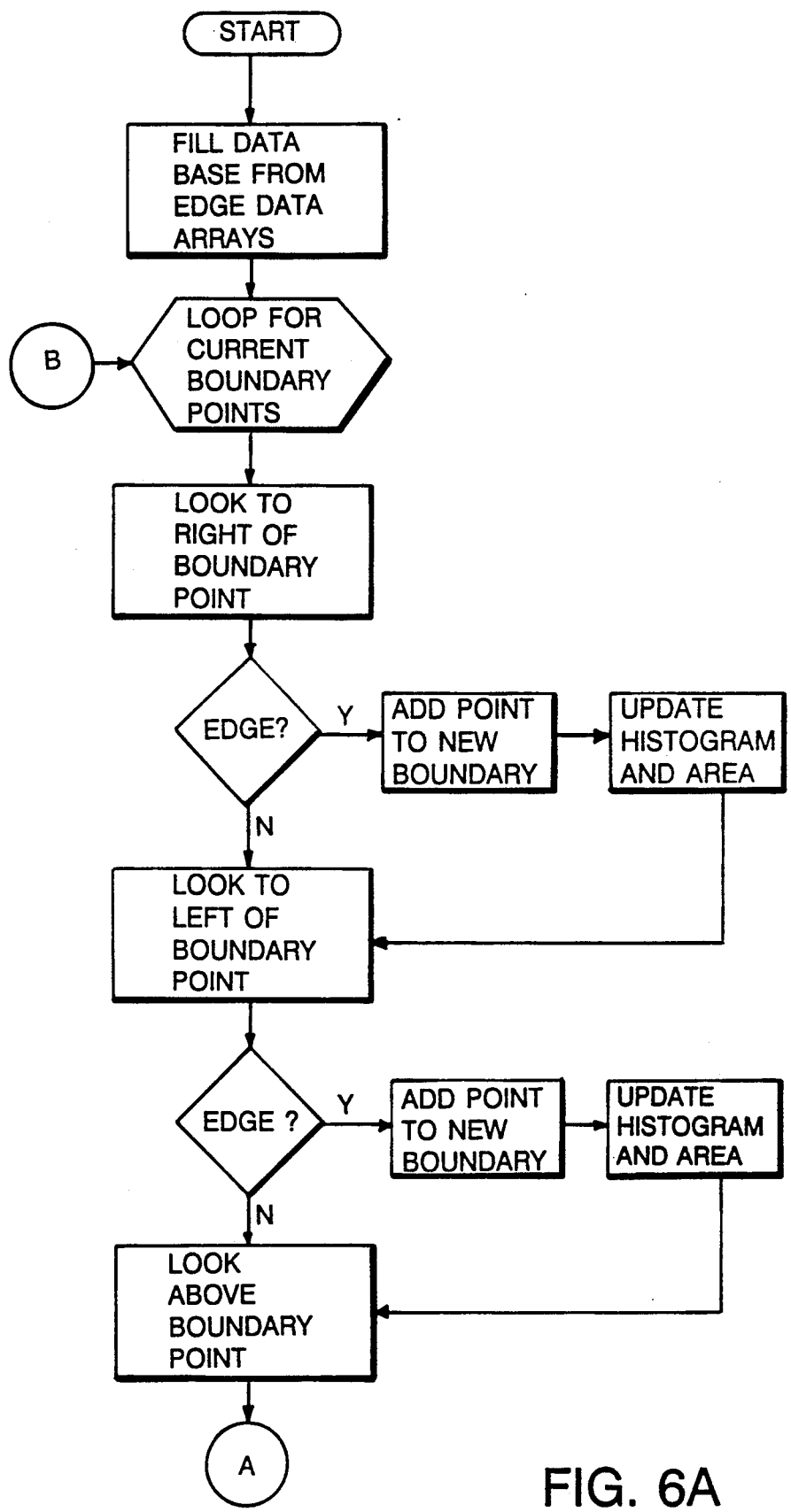
Figure 6B:
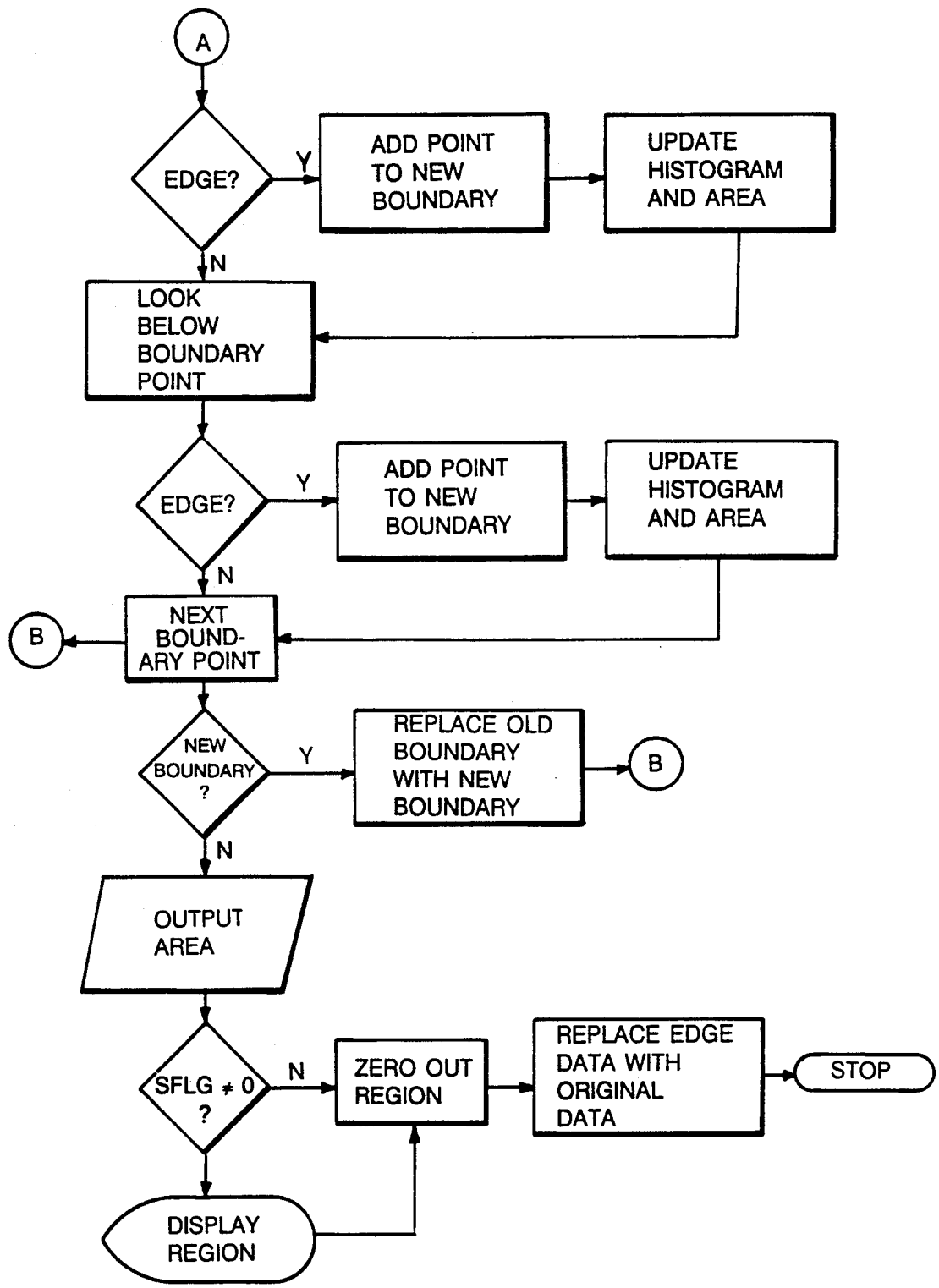
Figure 7A:
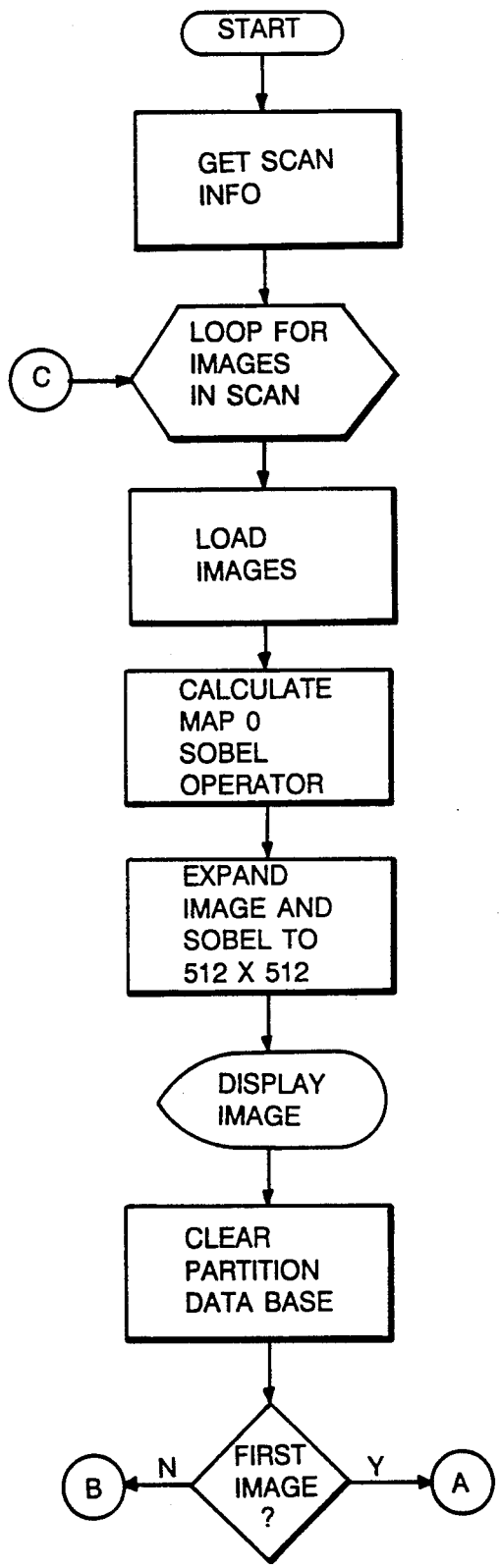
Figure 7B:
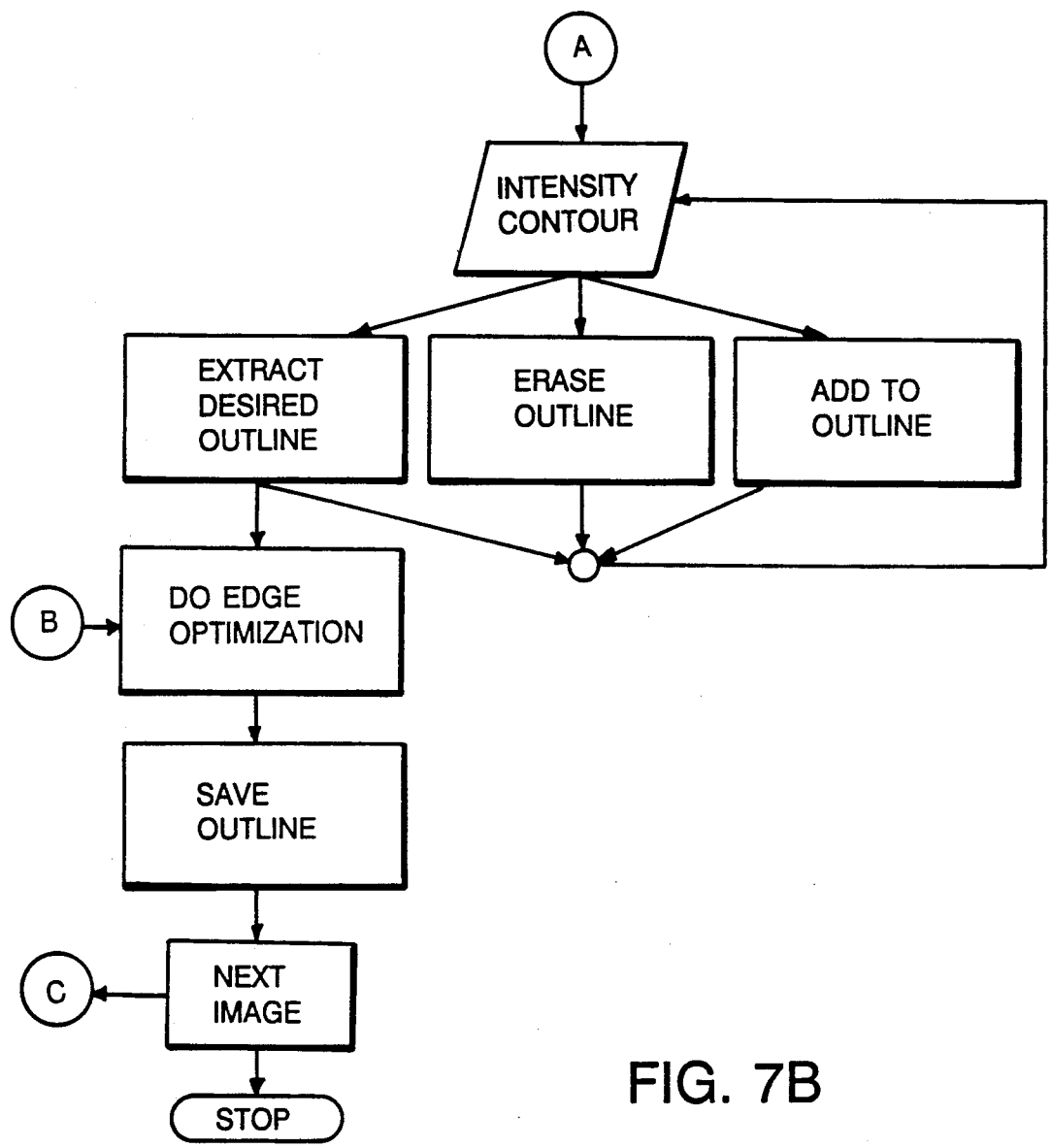

The final step in the morphometric analysis is to compute the volumes of the regions within the selected outlines (in some cases the volume of a region is determined by subtracting the volume of one or more interior regions therefrom). The volumes are determined using the AREAS program, which calculates for each outline the sum of all the areas enclosed on that outline in all the slices. The enclosed areas are already stored in memory, having been computed, by subprogram FILLP, when the outlines were generated for each slice. FILLP differs from HFILL2 (the flow chart for which is shown in FIGS. 6A, 68) in that the histogram computation is not performed (as it is only needed for producing the initial intensity-contour-based outline). FILLP and HFILL2 simply fill the region within a given outline, counting pixels and generating a histogram (in the case of HFILL2) as the filling proceeds.

To facilitate analysis, the neocortical regions with subjacent white matter have been divided into what are termed precallosal, paracallosal, and retrocallosal regions.

The precallosal region is defined as that in the slices anterior to and not including the slice at which the corpus callosum is first visualized.

The paracallosal is divided into superior and inferior regions, each of which are, in turn, divided into anterior and posterior portions, resulting in four quadrants.

The superior paracallosal (frontal and parietal above sylvian fissure) is defined as the slices which include visualization of the corpus callosum in continuum, superiorly extending from an arbitrary line drawn connecting the white matter interface of the inferior circular insular sulcus, and the optic tract, minus the volume of the insular cortex between the circular insular sulci, and the claustrum. The anterior superior paracallosal segment is defined as those paracallosal slices anterior to but not inclusive of visualization of the third ventricle. The posterior superior paracallosal segment is defined as those paracallosal slices inclusive of and posterior to visualization cf the third ventricle.

The inferior paracallosal (temporal and insular below sylvian fissure) is defined as the slices include visualization of the corpus callosum in continuum, inferior to the arbitrary line connecting the inferior circular insular solcus and the optic tract, and including, in addition, the volume of insular cortex and claustrum. The anterior inferior paracallosal segment is defined as those paracallosal slices anterior to but not inclusive of visualization of the third ventricle. The posterior inferior paracallosal segment is defined as those paracallosal slices inclusive of and posterior to visualization of the third ventricle.

The retrocallosal segment is defined as those paracallosal slices inclusive of and posterior to visualization of the third ventricle.

Results

The preferred embodiment has been used to make volumetric measurements on the brains of seven normal volunteers, aged 16 to 32 years, defined as having a normal head circumference and neurologic examination. The Siemens FLASH (Fast Low Angle Shot) three-dimensional gradient echo pulse sequence was performed on each subject on a Siemens 1.0 Tesla Magnetom MR System (TR=40 MSEC, TE=15 MSEC, SL=3.1 MM). The image data (63 planar slices or sets of tomographic data) were transferred by magnetic tape onto the Digital Equipment Corporation VAX 11/750 computer system for image processing. The outline selection algorithms described earlier were used to select outlines, i.e., to segment the image into specific regions or features of neuroanatomic interest, e.g., cerebral hemispheres, cerebral cortex, cerebral white matter, ventricular system, individual basal ganglia, diencephalon, cerebellum, and brain stem. The absolute volume of each region was automatically calculated by the software, for each slice, according to the following:

(slice thickness) × (area/pixel) × (pixels/outline)

The resulting volumes for each slice were summed to produce the overall volume of the region.

Published normative data from fresh (unfixed) brain specimens (mean age=63.5 years) are available for the following structures: cerebral hemispheres (Paul F. Z Anat Entwickl-Gesh, 133, 325, 1971); cerebral cortex [Kretschmann H. J., A. Schleicher, J. F. Grottschreiber, W. Kullman. J. Neurol. Sci., 43, 11, 1979]; whole brain, ventricular system, and cerebellum (Wessely, W., J. Hirnforsch, 12, 11, 1970). The mean volumetric norms for the cerebral hemispheres and cortex were subsequently age adjusted to 25 years, according to the linear hemispheric volume shrinkage rate of 2.15% per decade (Miller, A.K.H., R. L. Alston, Jan Corsellis. Neuropath. Appl. Neurobiol., 6, 119, 1980). The absolute volumes from the seven MRI data sets were averaged and the percent deviation from published norms for each substructure was calculated. The results were as shown in Table 1 (where the asterisks indicate that fresh volumes were not available).

MRI scans were also performed on a phantom containing 1,000 cc (plus or minus 5 cc) of doped water (1 gram $CuNO_2$:1,000 grams $H_2O$). The Siemens FLASH three-dimensional gradient echo pulse sequence was utilized on a 1.0 Tesla Siemens Magnetom MR System at the following slice thicknesses: 1.6 mm, 3.1 mm, and 6.3 mm (TR=60 MSEC, TE=15 MSEC). The Siemens inversion recovery sequence was used to obtain contiguous 8 mm and 5 mm slices (TR=5250 MSEC, TI=250 MSEC, TE=35 MSEC).

TABLE 1

| Anatomic Region | Normal Subjects | | Percent Deviation |
|---|---|---|---|
| | MRI-Based Volume Mean [±SD], $cm^3$ | Normal Fresh* Volume Mean [±SD], $cm^3$ | |
| Whole Brain | 1343.4 ± 126.9 | 1370.6 ± 139.6 | 1.9 |
| Cerebral Hemispheres | 1181.9 ± 119.7 | 1197.6 ± 125.6 | 1.3 |
| Cerebral Cortex | 762.7 ± 53.2 | 772.0 | 1.2 |
| Cerebral White Matter | 400.6 ± 72.1 | * | — |
| Ventricular System | 15.8 ± 4.9 | 14.4 ± 6.3 | 9.7 |
| Caudate | 6.7 ± 1.7 | * | — |
| Putamen | 8.5 ± 1.2 | * | — |
| Globus Pallidus | 2.1 ± 0.2 | * | — |
| Diencephalon | 19.2 ± 2.4 | * | — |
| Cerebellum | 140.9 ± 17.1 | 142.0 ± 16.0 | 1.0 |
| Brain Stem | 20.9 ± 3.2 | * | — |

The external borders of the phantom were delineated on each planar image using the automated intensity contour mapping algorithm, and the absolute volumes of the phantom were calculated, as described in earlier studies on normal patients, for each slice thickness. The MRI-based volume of the phantom at each slice thickness was compared to the measured volume, and the percent error was calculated. The results were as shown in Table 2.

TABLE 2

| Slice Thickness | Phantom Determination | |
|---|---|---|
| | MRI-Based Volume | Percent Error |
| 8.0 mm | 1096 | 9.6 |
| 6.3 mm | 1081 | 8.1 |
| 5.0 mm | 1064 | 6.4 |
| 3.1 mm | 1052 | 5.2 |
| 1.6 mm | 1045 | 4.5 |

Other embodiment of the invention are within the following claims. For example, broad aspects of the invention have application to other types of anatomical tomographic data than MRI.

| Software | |
|---|---|
| FINAL | Main program for producing initial outlines for a single plane of data. |
| LABELS | A listing containing the text strings used for labelling. |
| CNAMES | Converts a numerical image number into a character image number. |
| CONTRAST | Alters the display parameters of video monitor by resetting the output look-up tables; also sets in color overlay for highlighting outlines and other things; performs initialization of video monitor. |
| LNLOAD | Loads the outline files previously created. |
| IMLOAD | Reads the image file from the disk and loads a map of the image intensity information |
| EXPAND | Expands 256 × 256 format received on magnetic tape from NMR system to 512 × 512 used on monitor. |
| MXMN | Allows user to indicate the maximum and minimum dimension extent that the image occupies on the screen, to shortening running times. |
| MDISP | Displays menus. |
| MEVAL | Evaluates menu selections. |
| CONT2 | Computes initial outlines from intensity contour; produces all contours for chosen intensity level; performs interpolation to chose contour location in situations where chosen intensity levelis not present. |
| SCONT | Computes a single contour by progressing point by point from starting point; otherwise similar to CONT2 |

| Software | |
|---|---|
| CONTSUB | Used by SCONT to chose outline. |
| RAD | Performs a radial differential technique for choosing initial outline; useful for regions like the caudate nucleus, which borders on one side the white matter and on the other the ventricle; caudate being gray, ventricle black, and white matter white, makes it impossible to use intensity contour for choosing outline because one intensity level will not work for selecting both the gray to white and gray to black outlines; so RAD chooses the outline by deciding whether a pixel differs (either positively or negatively) from the intensity at the center of the region by some predetermined number of standard deviations (e.g., caudate nucleus might have an intensity of 100 on the 0-255 gray scale, and the outline might be chosen as that location where pixels reach a difference of 20 (i.e., either 80 or 120). |
| NEWINT | Does interpolation. |
| EDGEXT | From an image full of contours it extracts a specific contour selected by the user positioning the cursor within the region defined by the outline. |
| HFILL2 | Computes the area and calculates the histogram while filling up the area within a selected outline. |
| HDISP | Displays the histogram values generated by HFILL. |
| EDIT | Lets the user go through all of the outlines saved and allows him to delete any of them or modify the labels of the regions that they are outlining; EDIT is called in the NEXT IMAGE block of the flow chart for FINAL (FIG. 4). |
| SIEMTEXT | Displays the text file that is included with the MRI data received from the NMR system. |
| DISP | A combination of IMLOAD and EXPAND; loads the image and expands it to 512 × 512. |
| FILLP | Similar to HFILL2, but does not calculate histogram. |
| AUTO2 | Performs edge optimization using simple differential operator. |
| MODADJ | Used by AUTO2 to shift outline from initial location to final location chosen based on differential operator; similar to NEWMOD. |
| AUTO3 | Same as AUTO2 but uses Sobel edge enhancement operator instead of simple differential; calls NEWMOD instead of MODADJ. |
| REVIEW | Lets user scan through images and see the saved outlines. |
| AREAS | Goes through each of the slices for a set of MRI data, and adds up the areas within each outline, for use in computing volume of features enclosed by outlines. |

We claim:

1. A method of processing anatomical tomographic data of a patient to identify and map a selected anatomical feature or region and identify within said feature a zone of abnormal inhomogeneity in tissue composition, comprising the steps of processing said anatomical tomographic data to determine an outline of said selected anatomical feature and saving said outline, deriving from said tomographic data an intensity of points within said feature, comparing said intensities to a predetermined variance from the mean of an intensity distribution of a normal population for said feature, identifying said zone of abnormal inhomogeneity as including points with intensities more than said predetermined variance, applying a standardized coordinate system to said tomographic data to characterize said zone of abnormal inhomogeneity in terms of its projection within said standardized coordinate system, and performing quantitative volumetric measurement of said zone of abnormal inhomogeneity.

2. The method of claim 1 wherein said predetermined variance is a predetermined number of normal standard deviations from the mean of the distribution of the normal population.

3. The method of claim 2 wherein said number of standard deviations is two.

4. The method of claim 1 wherein said deriving step comprises deriving an intensity histogram for points within said feature of said patient.

5. The method of claim 4 wherein said method further comprises the step of comparing said intensity histogram for said feature of said patient to intensity histograms for said feature from normal individuals.

6. The method of claim 1 wherein said intensity is T1 weighted.

7. The method of claim 1 wherein said intensity is T2 weighted.

8. The method of claim 1 wherein said standardized coordinate system is a standardized three-dimensional coordinate system and the step of applying said coordinate system comprises locating the origin of said standardized three-dimensional coordinate system at a point directly visible in said topographic data, using a pair of reference landmarks directly visible in said tomographic data to supplement said origin and define said standardized coordinate system, and characterizing an anatomical landmark by projecting onto said standardized coordinate system applied to said tomographic data.

9. The method of claim 1 wherein said tomographic data comprises a plurality of contiguous slices through a living body and said quantitative volumetric measurement is based on the product of slice thickness, number of slices, and area of said zone of abnormal inhomogeneity.

* * * * *

UNITED STATES PATENT AND TRADEMARK OFFICE
CERTIFICATE OF CORRECTION

PATENT NO.   : 5,185,809

DATED        : February 9, 1993

INVENTOR(S)  : David N. Kennedy, Pauline A. Filipek, and Verne S. Caviness

It is certified that error appears in the above-identified patent and that said Letters Patent are hereby corrected as shown below:

Column 1, line 1, should read:

--This invention was made with government support under NS24279 awarded by the National Institute of Neurological Disorders and Stroke of the National Institutes of Health. The government has certain rights in the invention.--

Col. 1, lines 17, 28, and 64, "in vivo" should be --*in vivo*--.

Col. 1, line 23, "in vitro" should be --*in vitro*--.

Col. 4, line 8, "initiates" should be --initiate--.

Col. 5, lines 44-45, "point by point" should be --point-by-point--.

Col. 6, line 68, "edge predicting" should be --edge-predicting--.

Col. 7, line 9, "happen-", should be --happen--.

Col. 8, line 65, "cf" should be --of--.

UNITED STATES PATENT AND TRADEMARK OFFICE
CERTIFICATE OF CORRECTION

PATENT NO. : 5,185,809

DATED : February 9, 1993

INVENTOR(S) : David N. Kennedy, Pauline A. Filipek, and Verne S. Caviness

It is certified that error appears in the above-identified patent and that said Letters Patent are hereby corrected as shown below:

Col. 9, line 43, "Z Anat Entwickl-Gesh" should be --Z Anat Entwickl-Gesh--.

Col. 9, line 48, "J. Hirnforsch" should be --J. Hirnforsch--.

Col. 9, line 53, "Neuropath. Appl. Neurobiol." should be --Neuropath. Appl. Neurobiol.--.

Col. 10, line 66, "levelis" should be --level is--.

Col. 12, line 41, "topographic" should be --tomographic--.

Signed and Sealed this

Twenty-third Day of November, 1993

Attest:

Attesting Officer

BRUCE LEHMAN

Commissioner of Patents and Trademarks